United States Patent [19]

Detwiler et al.

[11] Patent Number: 5,321,492
[45] Date of Patent: Jun. 14, 1994

[54] DUAL FUNCTION READHEAD FOR A REFLECTANCE INSTRUMENT

[75] Inventors: Paul S. Detwiler, Elkhart; Andrew J. Dosmann, Granger, both of Ind.

[73] Assignee: Miles Inc., Elkhart, Ind.

[21] Appl. No.: 930,805

[22] Filed: Aug. 7, 1992

[51] Int. Cl.⁵ .................... G01N 21/01; G01N 21/84
[52] U.S. Cl. ........................ 356/73; 356/39; 356/446; 356/72; 250/341; 359/152; 128/633
[58] Field of Search ............. 356/39, 73, 446, 51, 356/153, 71, 73.1; 250/372, 227.25, 341; 359/152, 153, 157, 167; 128/633

[56] References Cited

U.S. PATENT DOCUMENTS

| | | | |
|---|---|---|---|
| 4,791,461 | 12/1988 | Kishimoto et al. | 356/446 |
| 4,952,057 | 8/1990 | Kamikawa et al. | 356/73.1 |
| 5,222,152 | 6/1993 | Fishbine et al. | 356/71 |

Primary Examiner—Vincent P. McGraw
Assistant Examiner—LaCharles P. Keesee
Attorney, Agent, or Firm—Roger N. Coe

[57] ABSTRACT

A dual function readhead for a reflectance instrument is located in a housing for the instrument. A first light source for emitting radiation for reflectance readings and transmitting data is mounted in the readhead. In addition, a first photodetector is mounted in the readhead for detecting or receiving reflectance readings. A format or interface access port is defined in the readhead. An interface is provided that includes a second photodetector for detecting data transmitted by the first light source. A microprocessor is also provided for decoding data received by the second photodetector. A second light source may also be included with the interface for transmitting commands or data to the first photodetector. Software for controlling the operation of the first light source and the first photodetector is also provided.

10 Claims, 1 Drawing Sheet

DUAL FUNCTION READHEAD FOR A REFLECTANCE INSTRUMENT

BACKGROUND OF THE INVENTION

A. Field of the Invention

The present invention relates to a new and improved reflectance instrument; and, more particularly, to a new and improved dual function optical readhead for photometric measurements of diffuse reflectance and/or full-duplex communication with peripheral devices.

B. Description of the Background Art

Whole blood glucose test strips have been used for many years by hospitals, doctors, and individual patients for monitoring glucose levels in patients' blood to determine the stages or status of diabetes and other ailments. The whole blood glucose test strips are used with a reflectance instrument or meter and a work station or other data processing equipment. Tests are conducted using the instrument, and the test results can be stored in a memory in the instrument along with time, date, patient information and operator information. Periodically, the test results are transmitted by a hard wire connection to the work station or the data processing equipment for processing.

Typically, a test is conducted by inserting a reacted test strip into a slot or access port in the instrument. Light from a light emitting diode in the instrument is directed at the reacted test strip. The light is then reflected back to a photodetector also in the instrument, and the reflected light is measured. The instrument includes software that converts the amount of measured reflected light to units of blood glucose by means of an algorithm.

A typical use of the reflectance instrument is for a nurse making his or her rounds in a hospital to test the blood of several patients and store the test data and patient information in the memory of the instrument. Upon the completion of the nurse's rounds, the reflectance instrument is coupled to a work station or other data processing instrument through a hard wire connection such as a cable. The collected test data and patient information are communicated to the work station and processed. Processing can include comparing accumulated data to earlier test data to determine a trend or a long term fluctuation in the glucose levels in the patient's blood. This information can be used to assist the doctors in diagnosis and treatment, and also to assist patients in the control of their disease.

Reflectance instruments typically have size limitations. It is preferred that the instruments be of a size to allow them to be carried easily by a patient. This encourages patients to carry the instrument on his or her person and to test the glucose level of their blood several different times during each day. The test data are maintained in the memory of the instrument, and the patient periodically visits his or her doctor whereupon the reflectance instrument is coupled to a work station or data processing machine in the doctor's office by a hard wire connection and data are transmitted for analysis. The size requirements are also important for nurses since they must carry the instrument through their rounds.

These size requirements make it difficult to incorporate additional circuitry or software in the instrument to accommodate desired features such as data transfer. The size of reflectance instruments could be maintained at a user friendly size if another form of communication or data transfer could be developed that did not require the software and hardware required by the current instruments.

A reflectance instrument can include an LED (light emitting diode) and a photodetector. The instrument operates by applying a drop of blood to a glucose strip. Reagents in the pads of the strip react with the blood resulting in a color corresponding to the glucose level. This strip is then inserted into an access slot or port in the readhead position of the instrument to position the reacted pads adjacent to the LED and the photodetector. The LED is then pulsed to radiate the reacted pads with light. Light reflected from a pad is detected by the photodetector. The photodetector current is converted to percent reflectance by the analog to digital converter and microprocessor circuitry. Percent reflectance is converted to glucose concentration (mg/dL). The glucose reading, date, time, operator, etc. can temporarily be stored in the instrument. These data are transferred via an interface through a cable to a work station where software is used to analyze a chronological data base for each patient. This means of communication and the related structural elements that are required significantly increase the size and cost of the system which includes the reflectance instrument, interface circuitry, connectors, cables, work station and/or data processing equipment.

Less cumbersome ways to communicate or transfer data have been tried in other industries. For example the Hewlett Packard 82240A computer printer can be used to receive data using infrared light.

It would be desirable to provide a way to communicate between a reflectance instrument and data processing equipment while maintaining the compact size of the reflectance instrument and minimizing the overall costs.

SUMMARY OF THE INVENTION

Briefly, the present invention is directed to a new and improved dual function readhead for a reflectance instrument that measures analyte levels, e.g. glucose, cholesterol, etc. in whole blood or similar chemistry. The readhead of the present invention is part of an overall reflectance instrument and includes a first light source, e.g. a light emitting diode (LED), positioned adjacent to an access slot or aperture in the readhead into which a test strip may be inserted. A first photodetector is also mounted in the readhead adjacent to the access slot.

To determine the level of the analyte in a specimen drop of blood, a test strip with blood applied to one or more pads is inserted into the access slot. The first light source is activated and the reflected light is detected by a first photodetector. Software is included in the instrument to activate the light source and to convert the amount of reflected light measured by the photodetector to units of the analyte being measured.

The present invention also includes an interface that is provided with a second photodetector for detecting data transmitted by the first light source. The interface can further include a second light source. The interface is connected by a cable or other coupling to a work station or data processing equipment. Once test results have been gathered by the instrument, the software in the instrument can pulse the first light source to transmit the accumulated data to the second photodetector.

The data are then transmitted to the work station or data processing equipment.

The present invention allows reduction of the components of existing reflectance instruments having interfaces. Moreover, the size and manufacturing cost of the instrument are minimized by the use of an interface provided separately from the reflectance instrument which eliminates the need to add these components within the reflectance instrument.

BRIEF DESCRIPTION OF THE DRAWINGS

The above and other objects and advantages and novel features of the present invention will become apparent from the following detailed description of preferred embodiments of the invention illustrated in the accompanying drawings wherein.

Figure 1:
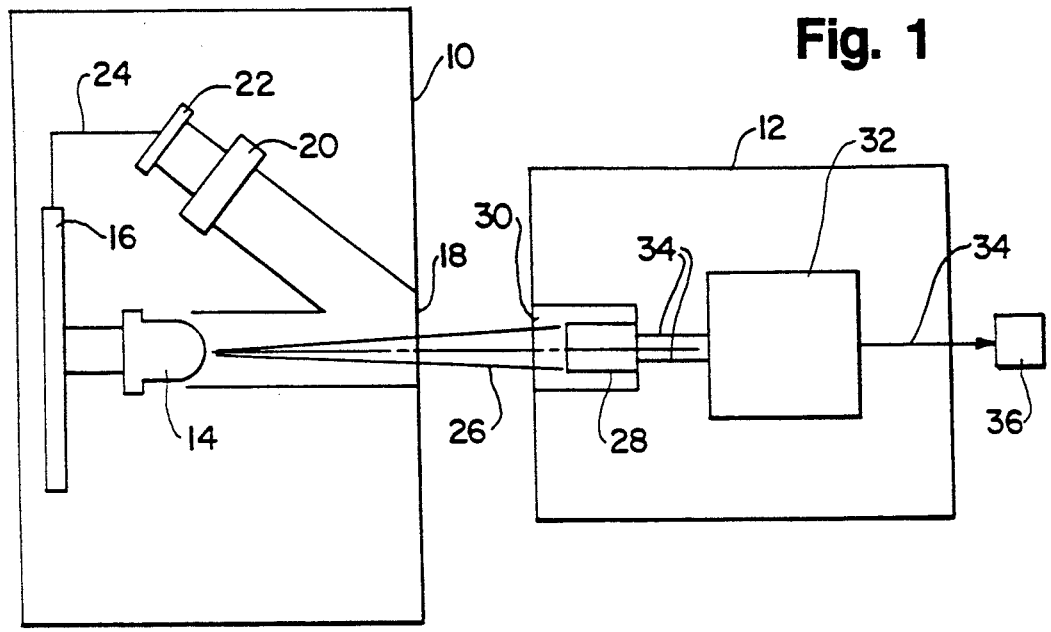
FIG. 1 is a schematic illustration of the readhead of a reflectance instrument and a simplex interface constructed in accordance with the principles of the present invention.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE PREFERRED EMBODIMENTS

Referring initially to FIG. 1, there is a schematic illustration of a readhead generally designated by the reference numeral 10 and an interface or decoding interface generally designated by the reference numeral 12. The readhead 10 includes a light source 14, e.g. an 840 nm (IR) light emitting diode (LED), that is modulated by a microprocessor 16 under software control. The light source 14 can be modulated for reflectance measurements to measure a reagent strip positioned adjacent an aperture 18 in the readhead 10. When used for reflectance measurements, light emanating from the light source 14 is reflected from pads on the reagent strip and detected by a photodetector 20, which is mounted in the readhead 10. The data collected by the photodetector 20 are converted to a binary number by an analog to digital counter 22 and transmitted to the microprocessor 16 by a wire, lead or similar structure 24.

When it is necessary for this data to be processed by a work station or other data processing equipment, the microprocessor 16 modulates the light source 14 to transmit a serial data stream of pulses in the form of light rays 26 directed toward the interface 12 that has been positioned adjacent to the aperture 18. The interface 12 includes a photodetector 28 positioned adjacent an aperture 30 in the interface 12. The data detected or gathered by the photodetector 28 are communicated to a microprocessor 32 by cables or conductors 34. The microprocessor 32 may be connected by a cable or similar conductor 34 to a personal computer or other data processing equipment 36 which processes the data to provide analysis and other information, such as a summary of the analyte levels in the blood of a patient taken over an extended period of time.

Through the combination of the readhead 10 and the interface 12, no additional circuitry or connecters are necessary. A software upgrade permits the microprocessor 16 to modulate the light source 14.

Figure 2:
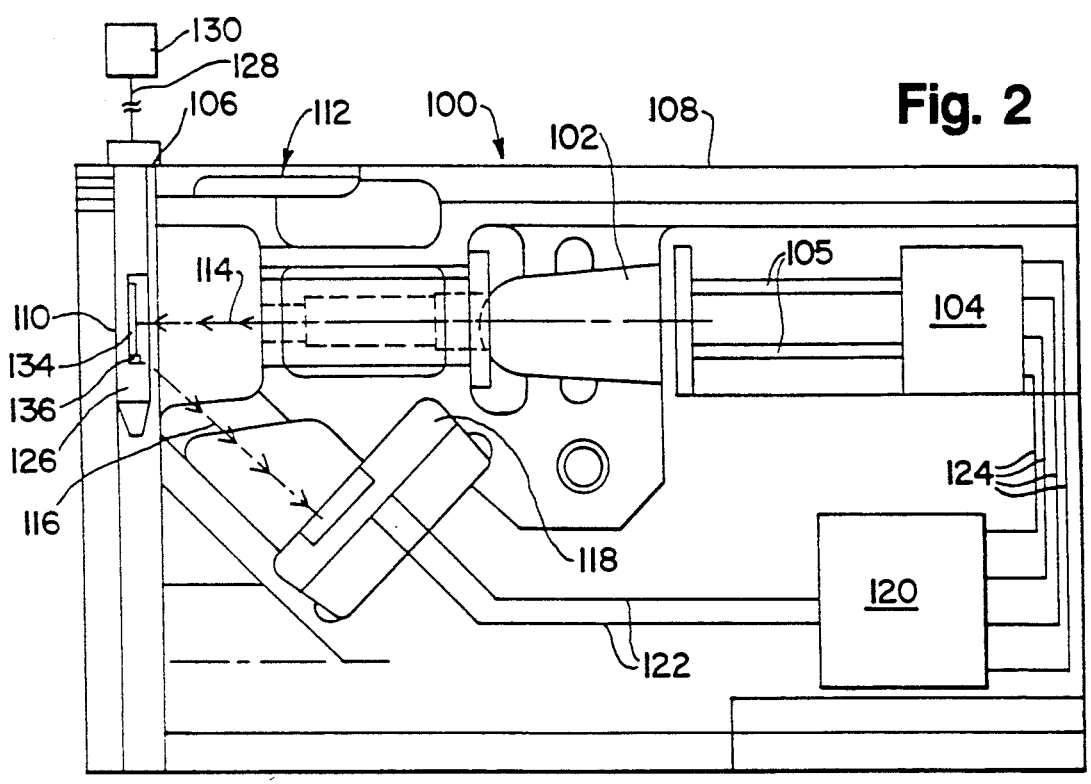
FIG. 2 is a schematic illustration of a readhead in a reflectance instrument in which a format including a second light source and photodetector, is inserted into an access slot in the readhead and is connected by a cable to a work station, and provides half or full duplex communication channel.

Turning now to FIG. 2, there is illustrated a reflectance instrument generally designated by the reference numeral 100. In contrast to the readhead 10 of FIG. 1 which is a simplex or one direction communication channel, the reflectance instrument 100 is duplex or bidirectional. The instrument 100 includes a light source 102 that is coupled by conductors 105 to and controlled and modulated by a microprocessor 104.

A format aperture or access port or opening 106 is provided in the casing 108 of the instrument 100. The opening 106 allows a reagent format or strip to be inserted into a slot 110 in a readhead 112 of the instrument 100.

When the instrument 100 is used to read a reagent strip (not shown) positioned in the slot 110, the instrument light source 102 is pulsed under the control of the microprocessor 104 and rays of light 114 emanate from the light source 102 to strike pads on the reagent strip. Light is reflected from the pads generally along a ray 116 to a photodetector 118 positioned in the instrument 100. The information collected by the photodetector 118 is communicated to an analog to digital converter 120 through cables, wires or similar elements 122. The analog to digital converter 120 includes a memory and upon command, the information stored in the memory of the analog to digital converter 120 can be communicated to the microprocessor 104 through cables, wires, or similar elements 124.

In order to process the data accumulated in the memory of the analog to digital converter 120, a format 126 is provided. The format 126 is of substantially the same dimensions as a reagent format or strip and can be inserted into the slot 110 through the aperture 106. The format 126 is coupled by a cable 128 to a personal computer, a work station, or similar data processing device 130. In using the format 126, it is desirable to construct the cable 128 to minimize capacitance and inductive reactance. Another approach would be to mount fiber optic cables in the format that would go back to the work station through the cable. Electronics in the workstation would then convert the light to an electrical signal.

The format 126 includes a photodetector 134 and a light source 136. When the format 126 is positioned in the slot 110, the photodetector 134 is optically aligned with the instrument light source 102, and the format light source 136 is optically aligned with the instrument photodetector 118. When it is desired to transmit data to the PC or data processing device 130, the data stored in the memory of the analog to digital converter 120 are communicated to the microprocessor 104. The instrument light source 102 is then modulated by the microprocessor 104 to transmit binary signals to the format photodetector 134.

The instrument light source 102 sends binary code by light intensities, on or off, to the photodetector 134. When the photodetector 134 detects a signal from the instrument light source 102, a voltage is generated that is transmitted to the work station, PC or data processing device 130 by way of the cable 128. This signal is then interpreted by the software of the work station, PC or data processing device 130.

The instrument 100 is a duplex instrument and during manufacturing the communication channel between the work station, PC or data processing device 130 and the instrument 100 can be used to load program code into the instrument 100. If the work station, PC or data processing device 130 is used to communicate with the reflectance instrument 100, the format light source 136 is driven by the work station, PC or data processing device 130 and is pulsed. These pulses are detected by the instrument photodetector 118, which develops voltages that are communicated to and interpreted by the microprocessor 104 through the analog to digital converter 120.

In addition, during manufacturing, existing code can be modified without opening the instrument case 108. If it is desirable to incorporate a software revision in a previously programmed instrument 100, this can be accomplished by the transmission of the binary code from the work station, PC or data processing device 130 to the format light source 136. The format light source 136 is pulsed to transmit binary signals to the instrument photodetector 118. This information is then transmitted or communicated to the microprocessor 104 via the wires or cables 122, through the analog to digital converter 120, to upgrade the software in the microprocessor 104.

The close positioning of the photodetector 134 and the instrument light source 102 make it possible to use a low cost wide bandwidth light source 136 and photodetector 134. In addition, this close positioning reduces the optical noise that can be picked up in the instrument 100. Also, due to the close coupling of the format 126, the instrument and format light sources 102 and 136, and the instrument and format photodetectors 118 and 134, this instrument and format light sources can be driven at a low current since they are in direct alignment with the light receiving photodetector. This helps to conserve the battery life of the instrument 100. The instrument 100 provides a dual function use of existing instrument components eliminating the need for additional chips, components, and connectors on the instrument side of the communications channel.

The present invention allows a single instrument 10 or 100 to be manufactured and each instrument may be easily adapted for a variety of purposes. Only minor changes to each instrument such as memory size and software need to be implemented to control the interface communication. Consequently, the same instrument can be used by an individual or a medical professional in a hospital or clinic. The difference, if any, in the instruments is only in the software. In the prior art, many different instruments are needed since the communication requirements for the instruments are different and this requires a variety of instrument sizes.

We claim:

1. A dual function readhead for a reflectance instrument, comprising:
   an instrument housing;
   a readhead (10) in said instrument housing;
   a first light source (14) in said readhead for emitting radiation for reflectance readings and transmitting data representative of said reflectance readings;
   a first photodetector (20) in said readhead;
   an interface (12), said interface including a second photodetector (28) for detecting said data transmitted by said first light source; and
   means (22) for decoding data received by said second photodetector.

2. The dual function readhead for a reflectance instrument claimed in claim 1 wherein said readhead includes an access slot (18) adjacent said first light source (14) and said first photodetector, said interface being of a size and shape to fit into said access slot.

3. The dual function readhead for a reflectance instrument claimed in claim 1 further comprising a conductor (34) connecting said interface (12) to said means (16) for decoding data.

4. The dual function readhead for a reflectance instrument claimed in claim 1 further comprising a second light source (136) in said interface.

5. The dual function readhead for a reflectance instrument claimed in claim 1 further comprising first means (16) for controlling said first light source for transmitting data.

6. A bidirectional readhead for a reflectance instrument, comprising:
   an instrument housing;
   a first light source (102) in said housing for emitting radiation for reflectance readings and transmitting data representative of said reflectance readings;
   a first photodetector (118) in said housing;
   a format aperture (106) in said housing, said first light source and said first photodetector being substantially adjacent said format aperture; and
   a format (126), said format including a second light source (136) and a second photodetector (134).

7. The bidirectional readhead for a reflectance instrument set forth in claim 6 wherein said format (126) is of a configuration allowing insertion into said format aperture (106) to position said second photodetector (134) in alignment with and adjacent to said first light source (102) and to position said second light source (136) in optical alignment with and adjacent to said first photodetector (118).

8. The bidirectional readhead for a reflectance instrument set forth in claim 6 further comprising a connector (128) connecting said format to data processing equipment (130).

9. The bidirectional readhead for a reflectance instrument set forth in claim 6 further comprising first means (104) for pulsing said first light source (102) for reflectance readings and for pulsing said first light source (102) to transmit reflectance data to said second photodetector (134).

10. The bidirectional readhead for a reflectance instrument set forth in claim 9 further comprising second means (120) for controlling said first photodetector (118) for collecting reflectance readings, processing said reflectance readings, and receiving transmissions from said second light source (136).

* * * * *

UNITED STATES PATENT AND TRADEMARK OFFICE
CERTIFICATE OF CORRECTION

PATENT NO.       : 5,321,492
APPLICATION NO.  : 07/930805
DATED            : June 14, 1994
INVENTOR(S)      : Paul S. Detwiler et al.

It is certified that error appears in the above-identified patent and that said Letters Patent is hereby corrected as shown below:

Column 3, line 55, after the word digital, replace the word "counter" with the word --converter--

Column 6, claim 1, line 8, after the word means, replace "(22)" with --(36)--

Column 6, claim 3, line 17, after the word means, replace "(16)" with --(36)--

Signed and Sealed this

Nineteenth Day of February, 2008

JON W. DUDAS
*Director of the United States Patent and Trademark Office*